US005824664A

United States Patent [19]
Schein et al.

[11] Patent Number: 5,824,664
[45] Date of Patent: Oct. 20, 1998

[54] SUPPRESSION OF HIV EXPRESSION BY ORGANIC THIOPHOSPHATE

[75] Inventors: Philip S. Schein, Bryn Mawr, Pa.; Thea Kalebic, Bethesda, Md.

[73] Assignees: U.S. Bioscience, Inc., West Conshohocken, Pa.; National Institutes of Health, The National Cancer Institute, Rockville, Md.

[21] Appl. No.: 37,633

[22] Filed: Mar. 26, 1993

[51] Int. Cl.$^6$ .......................... A01N 57/10; A01N 57/00; A61K 31/66; A61K 31/13

[52] U.S. Cl. ........................... 514/143; 514/75; 514/114; 514/665

[58] Field of Search ............................ 514/75, 114, 143, 514/665

[56] References Cited

U.S. PATENT DOCUMENTS

| 4,970,212 | 11/1990 | Nowicky | 514/279 |
| 5,218,088 | 6/1993 | Gorenstein et al. | 536/25.34 |

FOREIGN PATENT DOCUMENTS

WO90/14007  11/1990  WIPO.

OTHER PUBLICATIONS

Kalebic et al, J. Cell. Biochem., Supp 16E. p. 81 (1992).
Agostini et al., "Release of granulocyte–macrophage colony–stimulating factor by alveolar macrophages in the lung of HIV–1–infected patients", *The Journal of Immunology* 149(10): 3379–3385 (1992).
Baker and Wood, "Cellular antioxidant status and human immunodeficiency virus replication", *Nutrition Reviews* 50(1): 15–18 (1992).
Dröge et al., "HIV–induced cysteine deficiency and T–cell dysfunction—a rationale for treatment with N–acetylcysteine", *Immunology Today* 13(6): 211–214 (1992).
Grdina et al., "Protection against AZT–induced mutagenesis at the HGPRT locus in a human cell line by WR–151326", *Int. J. Radiation Oncology Biol. Phys.* 22: 813–815 (1992).
Ohnishi et al., "In vitro study on the antioxidant activities of amifostine (WR–2721)", *Proceedings of the American Association for Cancer Research* 33: Abstract 2503, p. 419 (1992).
Roederer et al., "N–acetylcysteine: A new approach to anti–HIV therapy", *Aids Research and Human Retroviruses* 8(2): 209–217 (1992).
Staal et al., "Glutathione deficiency and human immunodeficiency virus infection", *The Lancet* 339: 909–912 (1992).
Staal et al., "Intracellular glutathione levels in T cell subsets decrease in HIV–infected individuals", *Aids Research and Human Retroviruses* 8(2): 305–311 (1992).
Eck et al., "Metabolic disorder as early consequence of simian immunodeficiency virus infection in rhesus macaques", *The Lancet* 338: 346–347 (1991).
Grdina et al., "Protection by WR–151327 against late–effect damage from fission–spectrum neutrons", *Radiation Research* 128: S124–S127 (1991).

Green and Schein, "WR–151327: An orally active aminothiol chemoprotector for platinum and AZT toxicities in mice", *Proceedings of the American Association for Cancer Research* 32: Abstract 1906, p. 321 (1991).
Harakeh and Jariwalla, "Comparative study of the anti–HIV activities of ascorbate and thiol–containing reducing agents in chronically HIV–infected cells", *Am. J. Clin. Nutr.* 54: 1231S–1235S (1991).
Kalebic et al., "Suppression of human immunodeficiency virus expression in chronically infected monocytic cells by glutathione, glutathione ester, and N–acetylcysteine", *Proc. Natl. Acad. Sci. USA* 88: 986–990 (1991).
Rieckmann et al., "Activated B lymphocytes from human immunodeficiency virus–infected individuals induce virus expression in infected T cells and a promonocytic cell line, U1", *The Journal of Experimental Medicine* 173: 1–5 (1991).
Breen et al., "Infection with HIV is associated with elevated IL–6 levels and production", *The Journal of Immunology* 144(2): 480–484 (1990).
Fauci, "Cytokine regulation of HIV expression", *Lymphokine Research* 9(4): 527–531 (1990).
Harakeh et al., "Suppression of human immunodeficiency virus replication by ascorbate in chronically and acutely infected cells", *Proc. Natl. Acad. Sci. USA* 87: 7245–7249 (1990).
Kubota et al., "2,3 Dimercapto–1–Propanol inhibits HIV–1 tat activity, viral production, and infectivity in vitro", *Aids Research and Human Retroviruses* 6(7): 919–927 (1990).
Odeh, "The role of tumour necrosis factor–α in acquired immunodeficiency syndrome", *Journal of Internal Medicine* 228: 549–556 (1990).
Poli et al., "Interleukin 6 induces human immunodeficiency virus expression in infected monocytic cells alone and in synergy with tumor necrosis factor α by transcriptional and post–transcriptional mechanisms", *The Journal of Experimental Medicine* 172: 151–158 (1990).
Staal et al., "Intracellular thiols regulate activation of nuclear factor κB and transcription of human immunodeficiency virus", *Proc. Natl. Acad. Sci. USA* 87: 9943–9947 (1990).
Buhl et al., "Systemic glutathione deficiency in symptom-free HIV–seropositive individuals", *The Lancet* II: 1294–1298 (1989).

(List continued on next page.)

*Primary Examiner*—Leon B. Lankford, Jr.
*Assistant Examiner*—Francisco C. Prats
*Attorney, Agent, or Firm*—Pennie & Edmonds LLP

[57] ABSTRACT

Chronic HIV infection is treated by administering to a subject an organic thiophosphate alone or in combination with another anti–HIV or anti–AIDS drug. The organic thiophosphate is preferably WR 151327, a compound with antioxidant and free radical scavenging activities, or a functional derivative or analogue thereof. WR 151327 suppresses induction of HIV expression in chronically infected cells mediated by cytokines such as TNFα and GM-CSF. Pharmaceutical compositions comprising at least one organic thiophosphate in combination with one or more anti–HIV or anti–AIDS drugs are also disclosed.

24 Claims, 8 Drawing Sheets

OTHER PUBLICATIONS

Clouse et al., "Viral antigen stimulation of the production of human monokines capable of regulating HIV1 expression", *The Journal of Immunology* 143(2): 470–475 (1989).

Eck et al., "Low concentrations of acid–soluble thiol (cysteine) in the blood plasma of HIV–1–infected patients", *Biological Chemistry Hoppe–Seyler* 370: 101–108 (1989).

Kharazmi et al., "Interleukin 6 primes human neutrophil and monocyte oxidative burst response", *Immunology Letters* 21: 177–184 (1989).

Meister, "On the biochemistry of glutathione", *Glutathione Centennial*, Academic Press, Inc., pp. 3–21 (1989).

Merrill et al., "Interleukin–1 and tumor necrosis factor $\alpha$ can be induced from mononuclear phagocytes by human immunodeficiency virus type 1 binding to the CD4 receptor", *Jounal of Virology* 63(10): 4404–4408 (1989).

Nakajima et al., "Induction of IL–6 (B cell stimulatory factor–2/IFN–$\beta_2$) production by HIV", *The Journal of Immunology* 142(2): 531–536 (1989).

Poli et al., "Interferon–$\alpha$ but not AZT suppresses HIV expression in chronically infected cell lines", *Science* 244: 575–577 (1989).

Roux–Lombard et al., "Purified blood monocytes from HIV 1–infected patients produce high levels of TNF$\alpha$ and IL–1", *Clinical Immunology and Immunopathology* 50: 374–384 (1989).

Stanley et al., "Induction of expression of human immunodeficiency virus in a chronically infected promonocytic cell line by ultraviolet irradiation", *Aids Research and Human Retroviruses* 5(4): 375–384 (1989).

Folks et al., "Characterization of a promonocyte clone chronically infected with HIV and inducible by 13–phorbol–12–myristate acetate", *The Journal of Immunology* 140(4): 1117–1122 (1988).

Lähdevirta et al., "Elevated levels of circulating cachectin/ tumor necrosis factor in patients with acquired immunodeficiency syndrome", *The American Journal of Medicine* 85: 289–291 (1988).

Reddy et al., "Tumor necrosis factor and HIV P24 antigen levels in serum of HIV–infected populations", *Journal of Acquired Immune Deficiency Syndromes* 1: 436–440 (1988).

Willey et al., "In vitro mutagenesis identifies a region within the envelope gene of the human immunodeficiency virus that is critical for infectivity", *Journal of Virology* 62(1): 139–147 (1988).

Folks et al., "Cytokine–induced expression of HIV–1 in a chronically infected promonocyte cell line", *Science* 238: 800–802 (1987).

Mitsuya and Broder, "Strategies for antiviral therapy in AIDS", *Nature* 325: 773–778 (1987).

Steel et al., "Protection of mice against fission neutron irradiation by WR–2721 or WR–151327", *Radiation Research* 109: 469–478 (1987).

Klebanoff et al., "Stimulation of neutrophils by tumor necrosis factor", *The Journal of Immunology* 136(11): 4220–4225 (1986).

Meister et al., "Intracellular cysteine and glutathione delivery systems", Journal of the American College of Nutrition 5: 137–151 (1986).

Sigdestad et al., "A comparison of radioprotection from three neutron sources and $_{60}$Co by WR–2721 and WR–151327", *Radiation Research* 106: 224–233 (1986).

Cathcart et al., "Vitamin C in the treatment of acquired immune deficiency syndrome (AIDS)", Medical Hypotheses 14: 423–433 (1984).

Gorman et al., "Recombinant genomes which express chloramphenicol acetyltransferase in mammalian cells", *Molecular and Cellular Biology* 2(9): 1044–1051 (1982).

Yuhas, "Active versus passive absorption kinetics as the basis for selective protection of normal tissues by S–2–(3–aminopropylamino)–ethylphosphorothioic acid", *Cancer Research* 40: 1519–1524 (1980).

DeChatelet et al., "Effect of phorbol myristate acetate on the oxidative metabolism of human polymorphonuclear leukocytes", *Blood* 47(4): 545–554 (1976).

SUPPRESSION OF HIV EXPRESSION BY ORGANIC THIOPHOSPHATE

This invention was made, in part, with government support. Therefore, the government has certain rights in the invention.

1. INTRODUCTION

The present invention in the fields of virology and medicine relates to methods for treating HIV infection or AIDS based on inhibiting HIV expression in a chronically HIV infected subject by administering an organic thiophosphate agent, preferably WR 151327 or a functionally active derivative or analogue thereof. This agent may be given alone, or in combination with one or more anti-HIV or anti-AIDS drugs.

2. BACKGROUND OF THE INVENTION

2.1. HIV Infection and Aids

Human Immunodeficiency Virus (HIV), the etiological agent for AIDS (Acquired Immune Deficiency Syndrome), is a member of the lentiviruses, a subfamily of retroviruses. HIV integrates into the genome of the host. The viral genome contains many regulatory elements which control its replication in both resting and dividing cells. HIV infects predominantly cells of the immune system, thereby destroying the immune system and rendering the infected individual more susceptible to opportunistic infections and neoplasms. The progressive and irreversible dysregulation of the immune system causes a high mortality rate that approaches 100% over several years.

Preferential target cells for HIV are the CD4-bearing T lymphocytes, and cells of the mononuclear phagocytic lineage (Dalgleish, A. G. et al., *Nature* 312:763–767 (1984)), including blood monocytes, tissue macrophages, Langerhans cells of the skin and dendritic reticulum cells within lymph nodes. HIV is also neurotrophic, capable of infecting glial cells and macrophages in the central nervous system causing severe neurologic damage.

HIV is transmitted by parenteral inoculation and/or intimate sexual contact. It is estimated that about 2 million people in the United States are currently infected with HIV, and 5 to 10 million people are infected worldwide. Recent projections indicate that a majority of those now infected will develop AIDS within a seven year follow-up period. It is apparent that AIDS is an unprecedented threat to global health. The search for effective therapies to treat HIV infection and AIDS is of paramount importance.

2.2. Anti-HIV Drugs

Intensive efforts are currently under way to develop therapies to prevent or intervene in the development of clinical symptoms in HIV-infected individuals. For the most part, efforts have been focused on the use of nucleoside analogue drugs such as AZT (azidothymidine), and on other dideoxynucleoside derivatives such as ddA, ddT, ddI, and ddC. These drugs inhibit the viral enzyme, reverse transcriptase, thereby inhibiting synthesis of double stranded viral DNA. These drugs are known to have a number of serious adverse side effects, including bone marrow suppression and anemia (*New Engl. J. Med.* 317:185–191 (1987)

Drugs targeting other early steps of the viral life cycle are also being developed, such as soluble CD4 and dextran sulfate to inhibit binding of HIV to the cell membrane. Interferon-α is known to inhibit viral budding (Poli, G. et al. (1989) *Science* 244:575–577). Castanospermine may inhibit the processing of the viral glycoproteins. These drugs are still in early stages of testing.

2.3. Modulation of the Expression of HIV in Chronically Infected Cells

A number of cofactors can potentially trigger the progression of HIV infection towards fully systemic disease. For example, one triggering event may be diminished levels of natural antioxidants, which are important immunoregulators, including glutathione (GSH) and acid soluble thiols. A decreased level of antioxidants was found in plasma, peripheral blood monocytes and lymphocytes of HIV infected individuals (Eck, H. P. et al., (1989) *Biological Chem. Hoppe-Seyler* 370:101–108; Buhl, R. et al., (1989) *Lancet* ii:1294–1298; Staal, F. J. (1992) *Lancet* 339:909–912; Staal, F. J. et al., (1992) *AIDS Res. Human Retrovir.* 8:305–11). Lower levels of GSH have also been noted in pleural fluid of AIDS patients and HIV-seropositive individuals (Buhl et al. supra). In an animal model of AIDS, a decrease in plasma GSH was one of earliest detectable changes caused by infection with Simian Immunodeficiency Virus (Eck, H. et al. (1991) *Lancet* 338:346–347). Thus, a chronic state of oxidative stress may play a role in the clinical condition of HIV-infected individuals.

Pro-inflammatory cytokines such as tumor necrosis factor-α (TNFα), interleukin-6 (IL-6) and granulocyte/macrophage colony stimulating factor (GM-CSF) are known to be elevated in HIV-infected individuals (Lahdevirta, J. et al., (1988) *Amer. J. Med.* 85:289–291; Reddy, M. M. et al., (1988) *J. Acquired Immune Deficiency Syndrome* 1:436–440; Breen, E. C. et al. (1990) *J. Immunol.* 144:480–484; Rieckmann, P. et al., (1991) *J. Exp. Med.* 173:1–5; Nakajima, K. et al., (1989) *J. Immunol.* 142:531–536; Agostini, C. et al., (1992) *J. Immunol.* 149:3379–3385). These cytokines can activate expression of latent HIV in chronically infected cells in vitro (Folks, T. M. et al., 1987) *Science* 238:800–802; Fauci, supra) and cause release of reactive oxygen intermediates, thereby altering cellular redox potential (Klebanoff, S. J. et al., (1986) *J. Immunol.* 136:4220–4225; DeChatelet, L. R. et al., (1976) *Blood* 47:545–554; Karazmi, A. et al., (1989) *Immunol. Lett.* 31:177–184). Reducing agents (anti-oxidants) such as those mentioned above, suppress the expression of HIV in vitro (see below). Understanding the interactions between (a) substances which both activate HIV expression and induce oxidative stress, and (b) anti-oxidants, is not only important for our knowledge concerning the progression of HIV infections in vivo, but also serves as the basis for newer approaches for treating HIV infection (Fauci A. S., (1990) *Lymphokine Res* 9:527–531; Baker, D. H. et al. (1992) *Nutr. Rev.* 50:15–18; Roederer, M. et al., (1992) *AIDS Res. Human Retrovir.* 8:209–217; Staal, F. J., (1992) *Lancet* 339:909–912).

The present inventors and their colleagues, as well as others, have studied the effects of reducing agents on HIV expression in vitro. Their results show that the reducing agents GSH, glutathione ester and N-acetyl cysteine (NAC) suppressed the HIV expression induced by transcriptional inducers TNFα and 13-phorbol-12 myristate acetate (PMA), and a post-transcriptionally active cytokine, IL-6, in chronically HIV-infected cells (Kalebic, T. et al., (1990) *Proc. Natl. Acad. Sci. USA* 88:986–990; Poli, G. et al., (1990) *J. Exp. Med.* 172:151–8). This result suggests that cytokine-induced upregulation of HIV expression depends on the level of reducing agents in the environment.

Thus, alterations in cellular antioxidant status may play a critical role in triggering activation of HIV replication during chronic infection. Such changes in antioxidant status may be caused by relative glutathione deficiency (Staal, supra). The reducing environment in cells is maintained primarily by GSH which serves as a major cellular antioxidant and redox buffer (Meister, A. *GLUTATHIONE CENTENNIAL: MOLECULAR PROPERTIES AND CLINICAL APPLICATIONS,* Academic Press, New York, 1989, pp. 3–21). The transport of GSH into cells however is not efficient due to its degradation by a membrane bound GSH-transpeptidase (Meister, A. et al., (1986) *J. Amer. Coll. Nutr.* 5:137–151). Alternative pathways to restore a physiologic intracellular redox environment in HIV-infected cells have therefore been examined Harakeh, S. et al. (1991) *Am. J. Clin. Nutr.* 54:1231S–1235S; Harakeh, S. et al., (1990) *Proc. Natl. Acad. Sci. USA* 87:7245–7249; Cathcart, R. (1984) *Med. Hypoth.* 14:423–433; Kubota, S. et al., *AIDS Res. Human Retrovir.* 6:919–927 (1990)).

The compound known as WR 151327, having the chemical name 1-propanethiol-3-[[3-(methylamino)propyl]amino]-dihydrogen phosphothiorate, is a derivative of WR-2721 (amifostine; Ethyol®; ethanethiol, 2-[(3-aminopropyl)amino]-dihydrogen phosphate) which is readily transported into cells (Yuhas, J. (1980) *Cancer Res.* 40:1519–1524). WR 151327 is known to scavenge, and protect cells from, oxidative radicals (Sigdestad, C. P. et al., (1986) *Radiation Res.* 106:224–233; Grdina, D. J. et al., (1991) *Radiat. Res.* 128:S124–SI27). WR 151327 was found to decrease the bone marrow toxicity caused by the anti-retroviral drug AZT (Green, D. et al., (1991) *Proc. Amer. Assoc. Cancer Res.* 32:321) and to decrease the mutagenic effect of AZT (Grdina, D. J. et al., (1992) *Int. J. Radiation Oncology Biol. Phys* 22:813–815). However, the use of WR 151327 to inhibit HIV activation has not heretofore been disclosed.

3. SUMMARY OF THE INVENTION

The present invention relates to novel methods and pharmaceutical compositions for treating HIV infection, based on the observations by the present inventors that the organic thiophosphate compound WR 151327 acts as a potent suppressor of HIV expression induced in chronically infected by agents such as the cytokines GM-CSF and IL-6.

Thus, the present invention provides a method for treating a subject infected with HIV, comprising administering to the subject an effective amount of at least one organic thiophosphate capable of suppressing expression of HIV from a cell chronically infected with HIV.

In the above method, the organic thiophosphate is preferably WR 151327 or a functional derivative or analogue thereof.

In a preferred embodiment, the WR 151327 or functional derivative or analogue is administered orally, preferably in a dose of between about 20 mg and about 20 g per m$^2$ of body surface area of the subject, more preferably between about 500 and 1500 mg/m$^2$ body surface area.

In the above method, the WR 151327 or functional derivative or analogue may be administered intravenously, preferably by drip intravenous infusion, in a preferred dose range of between about 10 mg and 10 g per mg/m$^2$ of body surface area of the subject, more preferably between about 250 and 750 mg/m$^2$.

The present invention also provides a method for treating a subject infected with HIV, comprising administering to the subject a combination of:

(a) an effective amount of at least one organic thiophosphates capable of suppressing expression of HIV in a cell chronically infected with HIV; and (b) a second anti-HIV or anti-AIDS drug.

In the above method, the organic thiophosphate is preferably WR 151327 or a functional derivative or analogue thereof.

In yet another embodiment, the present invention is directed to a method for inhibiting the expression of HIV from a cell chronically infected with HIV, comprising exposing the cell to an effective amount of at least one organic thiophosphates capable of suppressing expression of HIV in a chronically infected cell. The organic thiophosphate is preferably WR 151327 or a functional derivative or analogue thereof. The exposing is preferably performed in vivo.

Also provided is a method for inhibiting the activation of HIV expression induced by an HIV-activating agent, such as a cytokine, including TNFα, GM-CSF or IL-6, in a subject chronically infected with HIV, comprising administering to the subject an effective amount of at least one organic thiophosphate capable of suppressing expression of HIV in a chronically infected cell. A preferred organic thiophosphate is WR 151327 or a functional derivative or analogue thereof.

Also provide herein is a pharmaceutical composition for treating a subject infected with HIV, comprising:

(a) an effective amount of at least one organic thiophosphate capable of suppressing expression of HIV in a cell chronically infected with HIV;

(b) one or more additional anti-HIV or anti-AIDS drugs; and (c) a pharmaceutically acceptable carrier or excipient.

The organic thiophosphate in the pharmaceutical composition is preferably WR 151327 or a functional derivative or analogue thereof.

The anti-HIV drugs of the pharmaceutical composition are preferably an anti-retroviral drug, most preferably AZT, ddI or ddC.

4. DESCRIPTION OF THE FIGURES

FIG. 5 is a graph showing densitometric quantification of HIV proteins obtained by scanning the autoradiogram shown in FIG. 2a.

FIG. 6 is a graph showing the effect of WR 151327 on HIV-LTR transcriptional activity. Cells of the human rhabdomyosarcoma cell line, RD, were transfected with HIV-LTR-CAT and 12 hours later, after washing, treated with WR 151327 (15 mM) for 24 hours. TNFα was added to the cells 8 hours after WR 151327. Cell extracts were prepared and chloramphenicol acetyltransferase (CAT) activity was measured. In the control study, the cells transfected with the same HIV-LTR-CAT construct were incubated without WR 151327 in the presence or absence of TNFα. Values of CAT activity are the mean ± SD of experiments performed in triplicate.

FIG. 7 is a graph showing that co-incubation of TNFα with WR 151327 (15 mM) for six hours at 37° C. does not alter HIV-inducing capacity. TNFα was incubated with WR 151327 and then added to U1 cells. 48 hours later supernatants were harvested and RT activity was measured. As controls, U1 cells were stimulated with TNFα which had been incubated alone under identical conditions and then added to the cells for the same period of time. A representative experiment is shown. Variability between three independent experiments was <15%.

5. DETAILED DESCRIPTION OF THE INVENTION

The present inventors have discovered, by monitoring reverse transcriptase (RT) activity, total HIV proteins and HIV-LTR-CAT transcriptional activity, that WR 151327 acts to inhibit HIV viral and protein expression in chronically infected cells in vitro. On this basis, they have conceived of the use of WR 151327 and functional derivatives or analogues thereof, in methods of treating HIV infection.

WR 151327 (chemical nomenclature: 1-propanethiol-3-[[3-(methylamino)propyl]amino]-dihydrogen phosphothiorate) can be depicted as follows:

WR 151327 is a thiophosphate reducing agent with oxygen-free radical scavenging capacity (Grdina et al., 1991, supra) which exerts its anti-HIV activity without killing cells or inhibiting their growth.

The present invention provides a method for treating HIV infection comprising administering to a subject in need thereof an effective amount of WR 151327) or a related organic thiophosphate which has similar activity in inhibiting the activation of HIV expression in cells persistently infected with this virus. Such inhibition blocks progression of the infectious process at a late stage of infection.

Because reducing agents such as NAC and ascorbate suppress HIV replication in acutely infected cells (Roederer, M. et al., Proc. Natl. Acad. Sci. USA 87:4884–4888 (1990); Harakeh, S. et al., 1990, supra), it is also contemplated that WR 151327, or a functional derivative or analogue thereof, is useful for treating acute HIV infection in a subject and can be used to inhibit HIV replication in acutely infected cells in vitro or in vivo.

Thus, the use of the compositions and methods of the present invention provides a broader approach to the treatment of HIV infection than offered by most currently used anti-HIV drugs, which target a specific stage of the viral life cycle.

As used herein, a functional derivative or analogue of WR 151327 is a related chemical compound which is also (1) a reducing agent, (2) a free radical scavenger and (3) shares the properties of inhibiting HIV expression in chronically infected cells without being cytotoxic or cytostatic to the cells.

One preferred analogue of WR 151327 is the compound designated WR 151326, a dephosphorylated free thiol form of WR 151327 having the chemical structure:

Other preferred analogues are S-ω(ω-aminoalkylamino) alkyl dihydrogen phosporothioates, which can also be depicted as:

wherein R is hydrogen or an alkyl group containing 1 to 7 carbon atoms and m and n independently have a value of from 2 to 6. One example of such an analogue is S-2-(3-aminopropylamino)ethyl dihydrogen phosphorothioate: $NH_2-(CH_2)_3-NH(CH_2)_2-S-PO_3H_2$.

The utility of an analogue or derivative of WR 151327 in a method according to the present invention can be evaluated by one of ordinary skill in the art without undue experimentation. Known methods are used to assess reducing activity (Meister, A. *GLUTATHIONE CENTENNIAL: MOLECULAR PROPERTIES AND CLINICAL APPLICATIONS*, Academic Press, New York, 1989) and oxygen free radical scavenging activity, which is assessed by chemical neutralization of free radicals in vitro (see, for example, Grdina, D. et al.., *Drug Metab. Rev.* 20:13–42 (1989)

To evaluate suppression of HIV expression, the subject compound may be tested, as exemplified below, for its capacity to inhibit stimulation of HIV expression in chronically infected cells such as U1 or ACH2 cells (Folks, T. M. supra). For stimulation of HIV expression, one can use a cytokine such as TNFα or GM-CSF, the activating agent PMA, or heat treatment (Folks, T. M. et al., supra; Folks, T. M. (1988) *J. Immunol.* 140:1117–1122).

The preferred subject of the present invention is the human, although the methods and compositions are useful for treating infections with viruses related to HIV, in other mammalian species, such as simian immunodeficiency virus infections in monkeys.

By the term "treating" is intended the administering to a subject of the HIV-suppressive compound of the present invention, preferably WR 151327 or a functional analogue or derivative thereof, for purposes which may include prevention of viral reactivation, amelioration of symptoms, or cure of the HIV infection and of AIDS.

The methods of the present invention comprise administration of a pharmaceutical composition which contains an effective amount of an HIV-suppressive agent which inhibits expression of HIV from chronically infected cells. The HIV-suppressive agent is preferably WR 151327, alone or in combination with one or more other drugs useful in the treatment of HIV infection. Also intended are methods and compositions comprising a mixture of more than one HIV-suppressive organic thiophosphate of the present invention.

The HIV suppressive organic thiophosphate or mixture may be administered alone, or in combination with one or more drugs intended to treat HIV infection or symptoms of AIDS. Examples of such additional drugs include the known anti-retroviral agents, for example, AZT, ddA, ddT, ddI, and ddC. Many additional anti-retroviral drugs known in the art which inhibit the activity of various HIV genes are included within the scope of this invention. Also included in such combination therapeutic methods are anti-retroviral peptides, an antibody specific for an epitope of HIV, soluble CD4 peptides, or immunotoxins (Vitetta, E. et al., *Science* 219:644–650 (1983); Pastan, I. et al., *Cell* 47:641–648 (1986); Olsnes, S. et al., *Immunol. Today* 10:291–295 (1989); Oeltmann, T. N. et al., *FASEB J.* 5:2334–2337 (1991)) comprising such antibodies or CD4 peptides. Antibacterial or anti-parasitic drugs, such as drugs directed to *Pneumocystis carinii* disease, and drugs for alleviating any symptoms associated with AIDS, are included within the scope of the combination treatment methods and compositions of the present invention.

Medicaments are considered to be provided "in combination" with one another if they are provided to the subject concurrently or if the time between the administration of each medicament is such as to permit an overlap of biological activity.

The pharmaceutical compositions of the present invention may be administered by any means that achieve their intended purpose. Amounts and regimens for the administration of WR 151327 or a functional derivative or analogue thereof can be determined readily by those with ordinary skill in the clinical art of treating HIV infections and AIDS.

It is understood that the dosage of WR 151327, or a functional derivative or analogue thereof, will be dependent upon the age, sex, health, and weight of the recipient, kind of concurrent treatment, if any, frequency of treatment, and the nature of the effect desired. An effective amount of the active compound of the present invention is any amount which would serve to inhibit activation of HIV expression in vivo. The ranges of effective doses provided herein are not intended to limit the inventors and represent preferred dose ranges. However, the most preferred dosage will be tailored to the individual subject, as is understood and determinable by one of ordinary skill in the art without undue experimentation.

Typical dosages are in the range of between about 10 mg and 20 g per $m^2$ body surface area. Preferred doses for oral administration are between about 20 mg and about 20 g per $m^2$ of body surface area, more preferably between about 500 and 1500 mg/$m^2$ body surface area. Preferred doses for intravenous administration are between about 10 mg and 10 g per mg/$m^2$ of body surface area, more preferably between about 250 and 750 mg/$m^2$.

In the methods of the present invention, administration of WR 151327 or its functional derivative or analogue, may be by parenteral routes, including intravenous, intramuscular, intraperitoneal, subcutaneous, transdermal or rectal routes. Alternatively, or concurrently, administration may be by the oral route. Oral administration is particularly desirable.

For oral administration, the active ingredient, preferably WR 151327 or a functional derivative or analogue thereof, may be a preparation in any dosage form capable of oral administration. Such dosage forms include tablets, hard or soft gelatin capsules, caplets, dragees, pills, tablets including coated tablets, and solutions including elixirs, suspensions, or syrups.

The present methods also include providing a liquid based dosage form of the active compound suitable for administration to a subject in need thereof. The liquid base may be any liquid capable of transporting the active ingredient into the body without disrupting the activity of the compound or harming the patient. A preferred base is an isotonic solution, which may also contain conventional additives such as sugars. These solutions are useful for both oral and intravenous administration.

Suitable injectable solutions include intravenous subcutaneous and intramuscular injectable solutions. The active compound may also be administered in the form of an infusion solution or as a nasal inhalation or spray.

For intravenous administration, the active compound is preferably administered by drip infusion in a buffered aqueous solution. The active ingredient may be administered in single or divided doses.

Suitable formulations for parenteral administration include aqueous solutions of the active compounds in water-soluble form, for example, water-soluble salts. In addition, suspensions of the active compounds as appropriate oily injection suspensions may be administered. Suitable lipophilic solvents or vehicles include fatty oils, for example, sesame oil, or synthetic fatty acid esters, for example, ethyl oleate or triglycerides. Aqueous injection suspensions that may contain substances which increase the viscosity of the suspension include, for example, sodium carboxymethyl cellulose, sorbitol, and/or dextran. Optionally, the suspension may also contain stabilizers.

The active compound of the present invention may be administered rectally in the form of suppositories.

In general, the preparation in which the active compound of the present invention is administered contains from about 0.1 to about 99 percent, preferably from about 25–85 percent, of active compound(s), together with a carrier or excipient. Suitable pharmaceutically acceptable carriers comprise excipients and auxiliaries which facilitate processing of the active compounds into preparations which can be used pharmaceutically. Suitable excipients are, in particular, fillers such as sugars, such as lactose, sucrose, mannitol, or sorbitol; cellulose preparations and/or calcium phosphates, such as tricalcium phosphate or calcium hydrogen phosphate; as well as binders such as starch paste made using, for example, maize starch, wheat starch, rice starch, potato starch, gelatin, gum tragacanth, methyl cellulose, hydroxypropylmethylcellulose, sodium carboxymethyl cellulose, and/or polyvinylpyrrolidone. If desired, disintegrating agents may also be added, such as the abovementioned starches as well as carboxymethyl starch, cross-linked polyvinyl pyrrolidone, agar, or alginic acid or a salt thereof, such as sodium alginate. Auxiliaries which can be used in the compositions according to the present invention include flow-regulating agents and lubricants such as silica, talc, stearic acid or salts thereof, and/or polyethylene glycol.

Having now generally described the invention, the same will be more readily understood through reference to the following example which is provided by way of illustration, and is not intended to be limiting of the present invention, unless specified.

6. EXAMPLE

Suppression of Induction of HIV Expression in Chronically Infected Cells by WR 151327

6.1. Material and Methods 6.1.1. Induction of HIV Expression in U1 Cells

The chronically infected U1 cell line was derived by infecting U937 promonocytic cells with HIV (Folks et al., 1988, supra). While the constitutive level of HIV expression in U1 cells is very low, an increase in HIV expression can be induced by various agents, including cytokines, phorbol esters and ultraviolet radiation (Folks et al., 1987, 1988, supra; Stanley, S. K. et al., (1989) *AIDS Res. Hum. Retrovir.* 5:375–384). In the present study, U1 cells were routinely maintained at a concentration of 2–5×10$^5$ cells/ml in RPMI-1640 medium (Bioproducts, Rockville, Md.) supplemented with 10% heat-inactivated fetal calf serum (FCS) (Biofluids, Rockville, Md.).

To assess the effect of WR 151327 on the induction of HIV expression, U1 cells plated in 96-well microtiter plates were pretreated with different concentrations of WR 151327 (2–15 mM) and then stimulated with PMA (10$^{-8}$M) (Sigma Chemical Co.), TNFα (100 U/ml) (Genzyme, Cambridge, Mass.) or GM-CSF (100 U/ml) (Genzyme, Cambridge, Mass.) for designated intervals. HIV expression was monitored by measuring the reverse transcriptase (RT) activity in the supernatants, as previously described (Willey, R. et al., (1988) *J. Virol.* 66:139–147).

WR 151327 (provided by U.S. Bioscience), a methylated derivative of WR-2721, an organic thiophosphate with anti-oxidative and radiation-protective properties (Sigdestad et al., supra; Grdina et al., 1991, supra; Steel, L. K. et al., (1987) *Radiation Res.* 109:469–478).

6.1.2. Reverse Transcriptase (RT) Assay

RT activity was measured in the supernatants of U1 cells according to the method of Willey et al. (supra). 10 μl aliquots of supernatant were added to 50 μl of a mixture containing poly(A), oligo(dT) (Pharmacia), MgCl$_2$, and $^{32}$P-labeled dTTP (Amersham), and incubated at 37° C. for 2 hours. Triplicate replicates, each containing 6 μl of the reaction mixture, were spotted onto DE81 filter paper (Whatman). The air-dried filters were washed in 1× SSC (0.15M NaCl/0.015M sodium citrate, pH 7) and 95% ethanol, dried, cut, and the uptake of the radioactive label was measured in a scintillation counter (Beckman LS 7000).

6.1.3. Western Blot Analysis

Western blots were used to measure the levels of HIV proteins in cell lysates of from U1 cells which has been pretreated with WR 151327 (15 mM) for 8 hours and then stimulated with TNFα (100 U/ml), GM-CSF (100 U/ml), or PMA (10$^{-8}$M) for 48 hours. The quantity of protein in each cell lysate was determined with a Bio-Rad protein quantification kit. Samples containing equal amounts of protein were loaded onto SDS 10–20% gradient polyacrylamide gel (Integration Separation Sciences, Hyde Park, Mass.) and fractionated by electrophoresis. The proteins were then transferred onto nitrocellulose filters and incubated with sera from AIDS patients containing anti-HIV antibodies recognizing the major viral proteins. After three washes, the filters were incubated with $^{125}$I-labeled protein A (200,000 dpm/ml) for 2 hours. Finally, the filters were washed, dried, autoradiograms made by exposure of x-ray film (Eastman Kodak). Densitometric quantification of HIV proteins was performed by scanning the autoradiogram in an Bio-Rad Model 620 video densitometer.

6.1.4. DNA Transfection and Transient Expression Assay

RD cells were transfected with HIV-LTR-CAT using calcium phosphate precipitation (Gorman C. M. et al., (1982) *Molec. Cell. Biol.* 2:1044–1051). 5×10$^5$ cells plated in 6-well tissue culture plates were incubated overnight at 37° C. and washed with fresh medium 3 hours prior to transfection. 1 μg of plasmid DNA and 4 μg of salmon sperm carrier DNA was used to transfect the cells in each well. After transfection, cells were incubated for 12 hours at 37° C., then washed and fed with fresh medium (RPMI 1640 supplemented with 10% fetal calf serum). WR 151327 (15 mM) was added to the fresh medium and cells were further incubated at 37° C. for an additional 24 hours. For TNFα stimulation, 100 U/ml were added to cultures 8 hours after adding fresh medium containing WR-151327, and the plates were incubated for an additional 16 hours. Cellular lysates were prepared by 3 freeze-thaw cycles.

In the control study, RD cells were transfected, washed 12 hours later, and incubated for the same period of time with medium in the absence of WR 151327 (with or without TNFα). Chloramphenicol acetyltransferase activity (CAT) was measured by diffusion assay. Transfection experiments were performed in triplicate and repeated at least twice.

6.2. Results

6.2.1. Decrease of RT Activity by WR 151327 in U1 Cells

Figure 2:
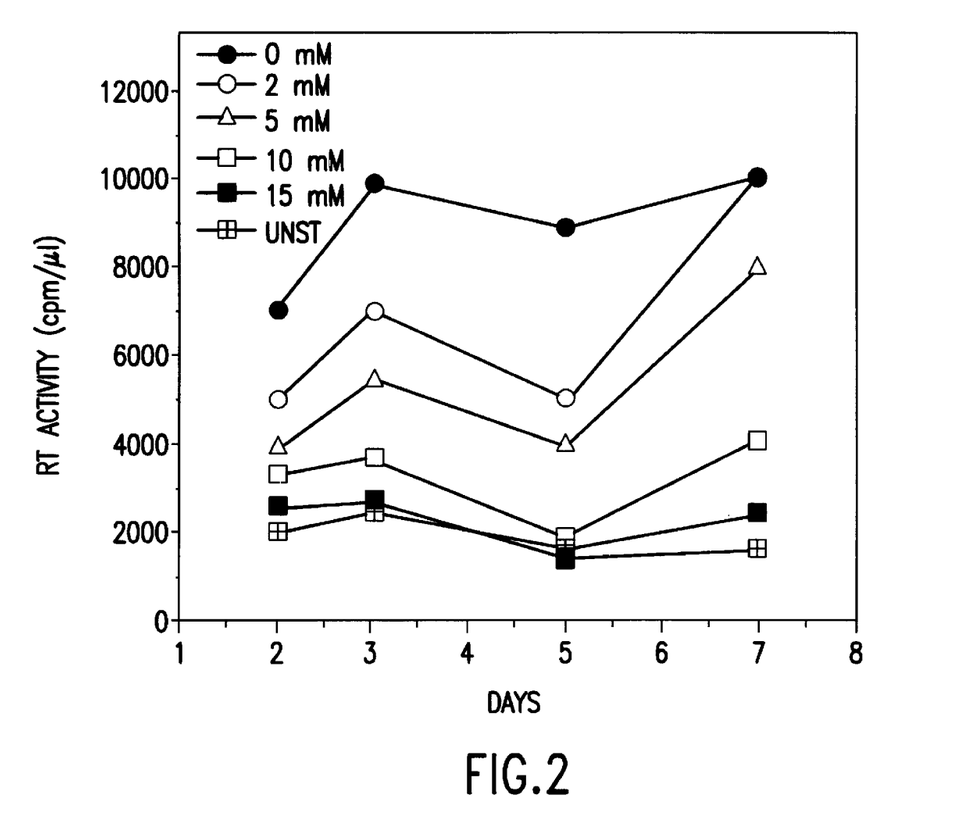
FIG. 2 is a graph showing the kinetics of suppression of RT activity by WR 151327 in U1 cells stimulated with TNFα (100 units per ml). See description of FIG. 1 for details.
Figure 3:
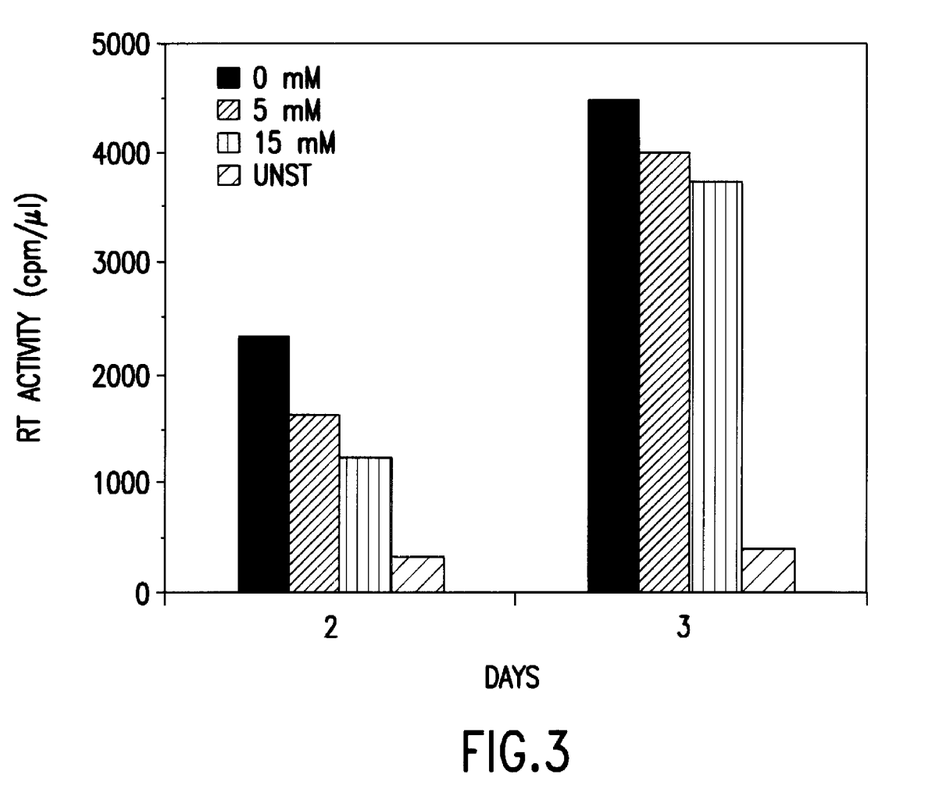
FIG. 3 is a graph showing the kinetics of suppression of RT activity by WR 151327 in U1 cells stimulated with PMA (10$^{-8}$M). See description of FIG. 1 for details.

A single pretreatment of cells with WR 151327 suppressed, in a dose-dependent fashion, the induction of RT activity mediated by GM-CSF (FIG. 1), TNFα (FIG. 2) or PMA (FIG. 3).

Figure 1:
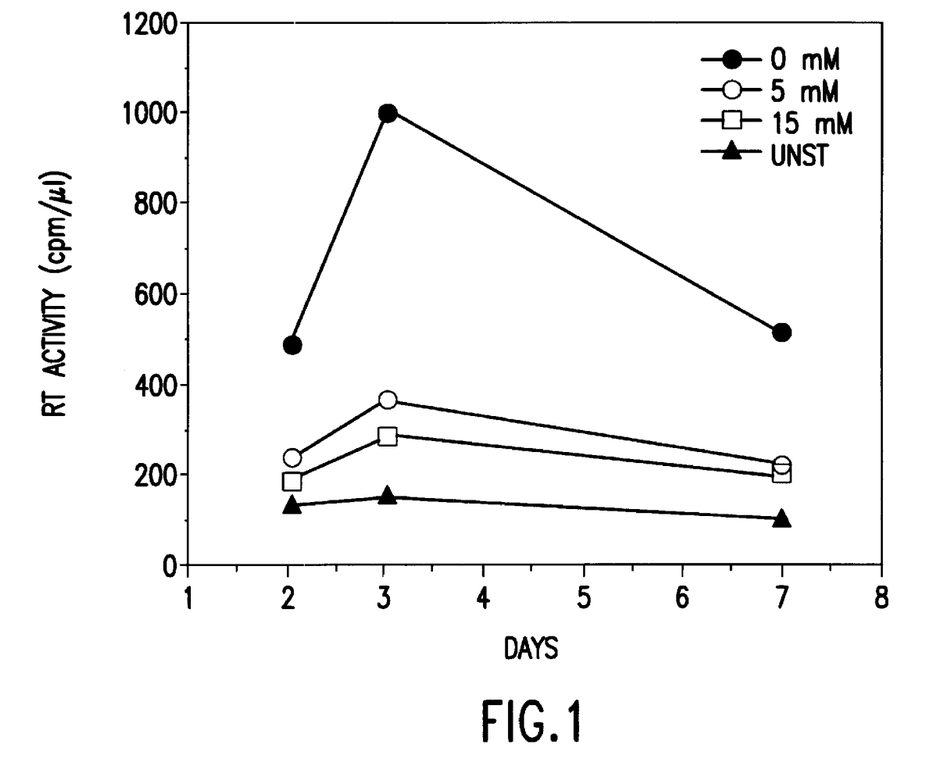
FIG. 1 is a graph showing the kinetics of suppression of reverse transcriptase (RT) activity by WR 151327 in U1 cells stimulated with GM-CSF (100 units per ml). Cells plated at a concentration of 4×10$^5$ per ml in fresh RPMI 1640 medium were pretreated for 8 hours at 37° C. with the indicated concentrations of WR 151327 and then stimulated with GM-CSF. Over a period of one week the culture supernatants were harvested at specific time intervals and RT activity was measured. A representative of three independent experiments is shown. Variability between experiments was <15%.

The maximal decrease of RT activity was approximately 80% in GM-CSF-stimulated U1 cells pretreated with 15 mM WR 151327. This concentration of WR 151327 achieved a comparable suppression of RT activity stimulated by TNFα. The maximal suppression of RT activity in PMA-stimulated U1 cells was 50%, detected after two days of incubation.

As shown in FIGS. 1–3, a single pretreatment with WR 151327 suppressed RT activity over a period of 5 days in TNFα- and GM-CSF-stimulated cells. In PMA-stimulated cells, the induction of RT activity was suppressed for a shorter period of time.

In the control groups, stimulation of U1 cells with TNFα (100 U/ml) or GM-CSF (100 U/ml) produced 5- to 10-fold increase in RT activity, while PMA (10$^{-8}$M) induced an approximately 15-fold increase of RT activity over baseline, consistent with previous reports. WR 151327 did not affect the baseline level of RT activity in unstimulated U1 cells at all concentrations tested (1–15 mM).

6.2.2. Effect of WR 151327 on Induction of HIV Protein Synthesis

Figure 4:
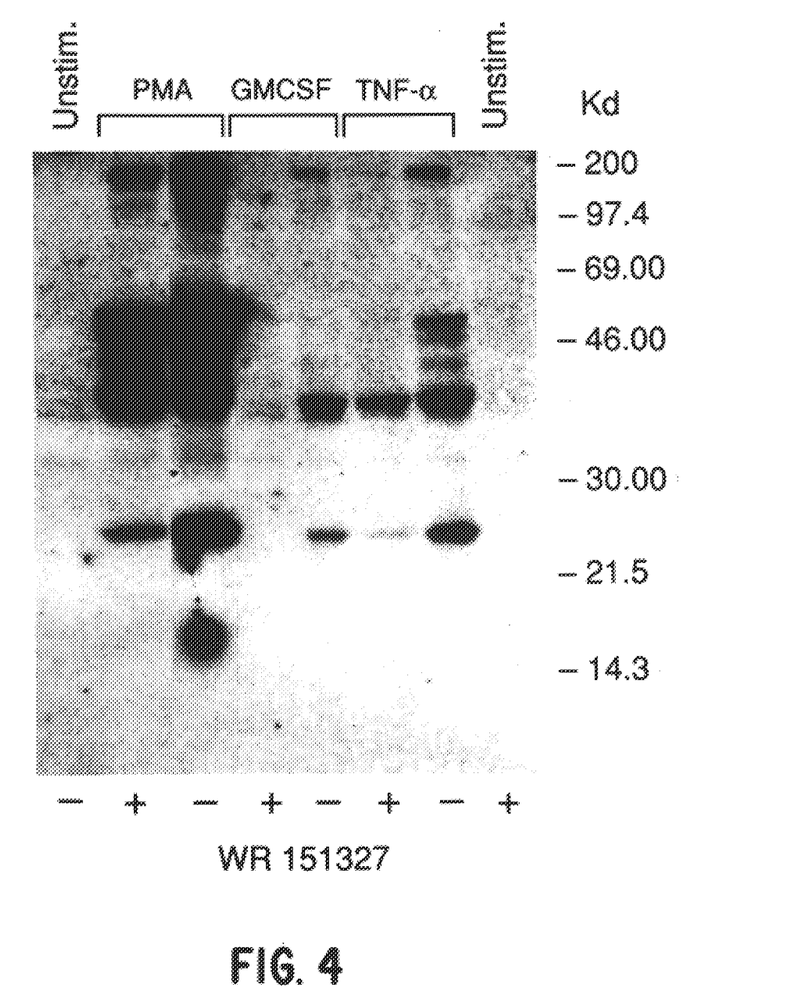
FIG. 4 is a Western blot showing the suppression in the level of HIV proteins by WR 151327 (15 mM) in U1 cells stimulated by TNFα, GM-CSF or PMA. Western blot analysis of total cellular lysates (75 μg protein per lane) from unstimulated cells (lane 1), TNFα-stimulated cells (lane 2), TNFα-stimulated cells pretreated with WR 151327 (lane 3), GM-CSF-stimulated cells (lane 4), GM-CSF-stimulated cells pretreated with WR 151327 (lane 5), PMA-stimulated cells (lane 6), and PMA-stimulated cells pretreated with WR 151327 (lane 7). The molecular mass (kDa) is indicated on the left. Results are representative of three independent experiments.

Pretreatment of U1 cells with WR 151327 (15 mM) inhibited the induction of total HIV proteins produced by TNFα, PMA and GM-CSF (FIG. 4). These results are consistent with the inhibition of RT induction by WR 151327 described above.

Figure 5:
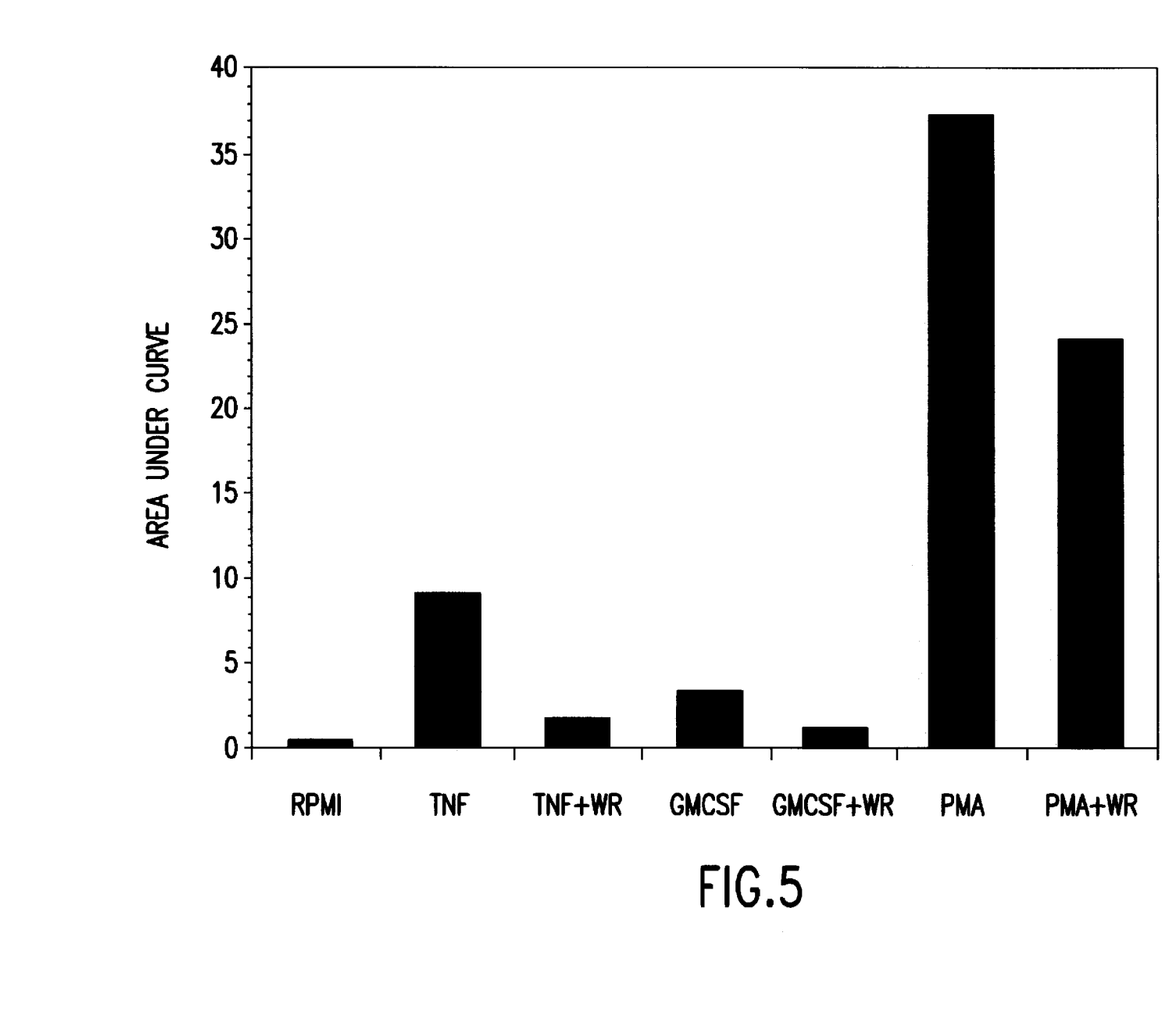

Scanning densitometry indicated that WR 151327 caused more than 50% suppression of total HIV proteins in GM-CSF-stimulated cells (FIG. 5). The induction of HIV proteins by TNFα was even more profoundly suppressed. In PMA-stimulated cells, WR 151327 decreased HIV proteins by approximately 30%.

As to time course, suppression of HIV protein synthesis by WR 151327 was detected in U1 cells after 48 or 72 hours of stimulation with TNFα, PMA, or GM-CSF.

Consistent with previous reports, only minimal levels of total HIV proteins were detected in unstimulated U1 cells. WR 151327 treatment did not change this baseline level of HIV proteins.

Examination of RT levels in the culture supernatants of the U1 cells which were being lysed for Western blot analysis indicated that RT activities were decreased to an extent comparable to the decrease in total HIV proteins.

6.2.3. WR 151327 Decreases the Level of Transcriptional Activity of HIV-LTR

It has been reported that N-acetyl cysteine suppressed the activation of HIV expression in lymphocytic cells by inhibiting the activity of the transcriptional factor NFκB which binds to HIV-LTR (Staal, F. J. et al., (1990) *Proc. Natl. Acad. Sci. USA* 87:9943–9947).

Studies were conducted to test whether the action of WR 151327 in suppressing HIV protein synthesis was accompanied by changes in the transcriptional activity of HIV-LTR in transiently transfected RD cells.

Twelve hours after transfection with HIV-LTR-CAT vectors, RD cells were washed, fresh medium containing WR 151327 (15 mM) was added, and the cells incubated for an additional 24 hours. This concentration of WR 151327, which maximally suppressed RT activity, was not toxic to the cells (see cell proliferation studies, below) and was therefore chosen to investigate effects on transcriptional activity of HIV-LTR-CAT, measured as CAT activity.

Figure 6:
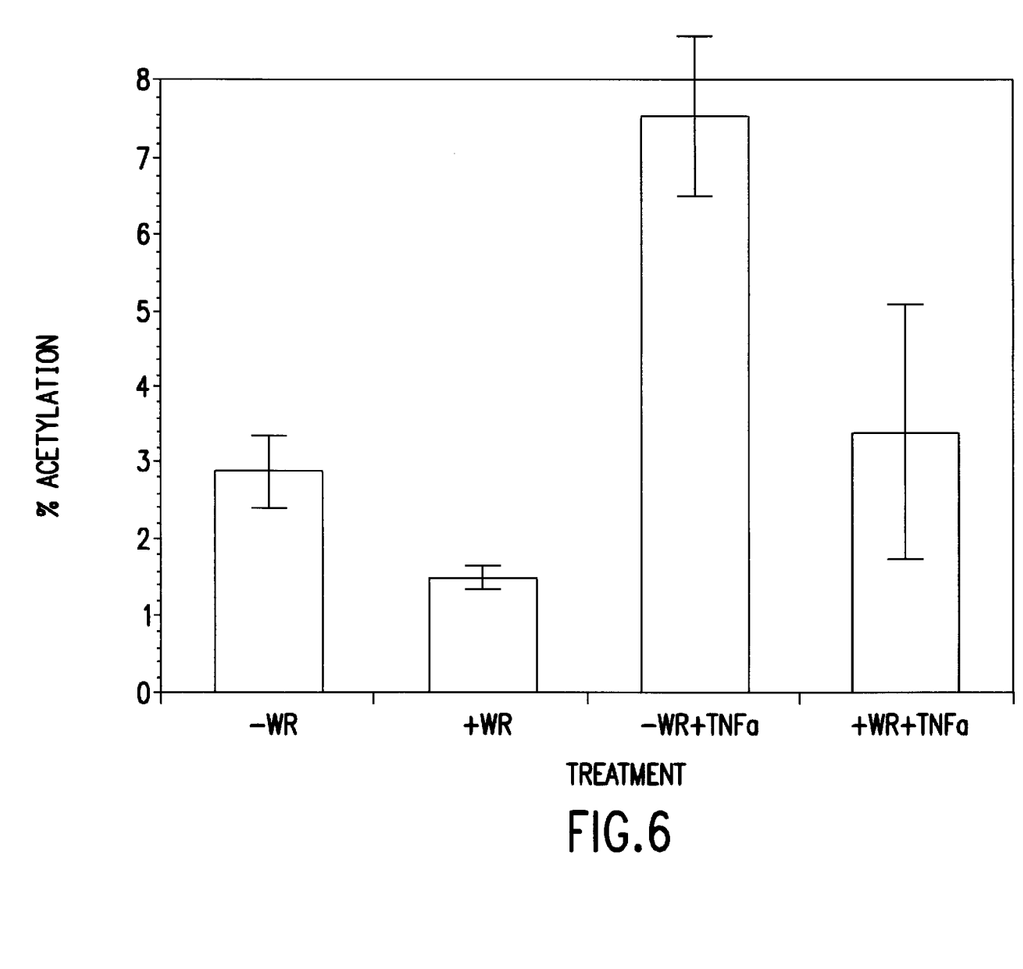

Transactivation of HIV-LTR-CAT was about 50% lower in transfected cells incubated for 24 hours with WR 151327 (15 mM) than in untreated control cells (see FIG. 6.

In addition, TNFα-mediated stimulation of transcription was also suppressed by about 50% by WR 151327 in transfected RD cells. A comparable suppression of CAT activity by WR 151327 was obtained in the monocytic cell line U937.

6.2.4. The Induction of HIV Expression by TNFα is Not Altered After its Incubation With WR 151327

Experiments were conducted to determine whether WR 151327 acted on TNFα directly, thereby reducing its capacity to induce the expression of HIV. TNFα was therefore incubated with WR 151327 (15 mM) for 6 hours at 37° C. After this incubation, TNFα was added to U1 cells and the stimulation of HIV expression was assessed by measuring RT activity in the supernatant 48 hours later.

Figure 7:
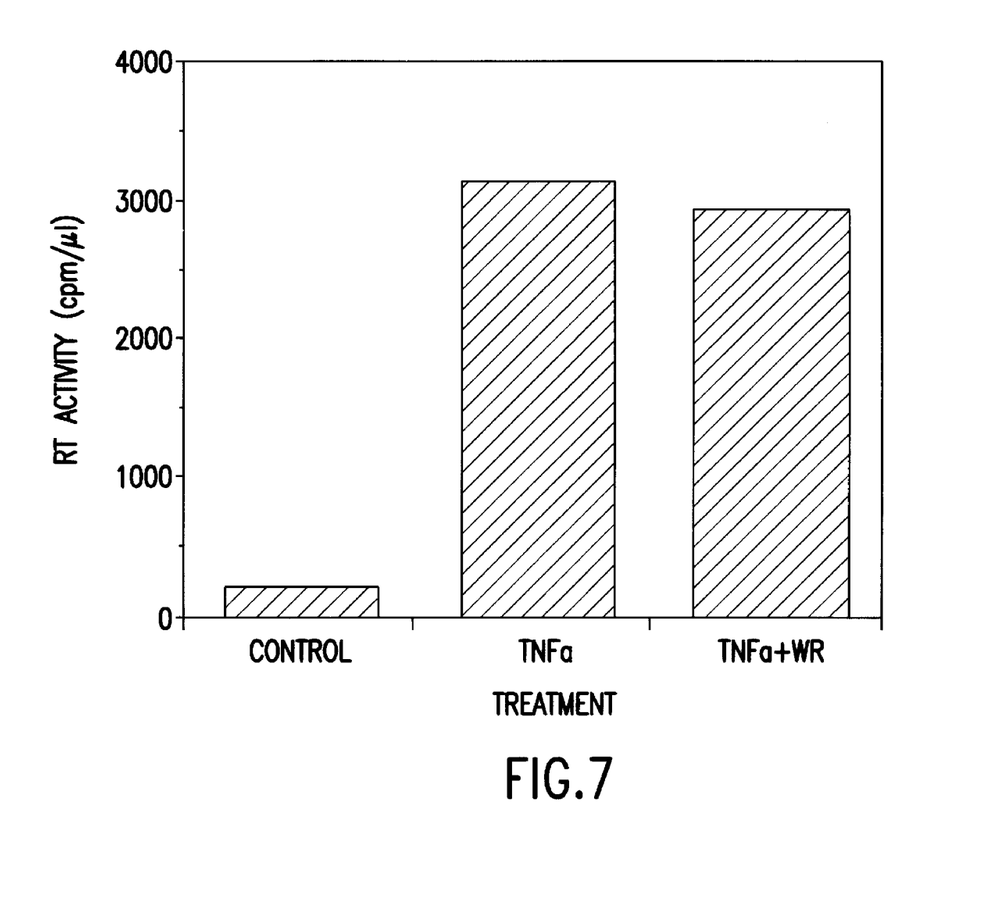

A 10-fold increase in the level of RT activity was produced by TNFα (100 U/ml) which had previously been incubated in vitro with WR 15132. This RT activity was result comparable to the RT activity induced by control TNFα (preincubated alone) (FIG. 7).

6.2.5. Proliferation of U1 Cells is Not Affected by WR 151327

Figure 8:
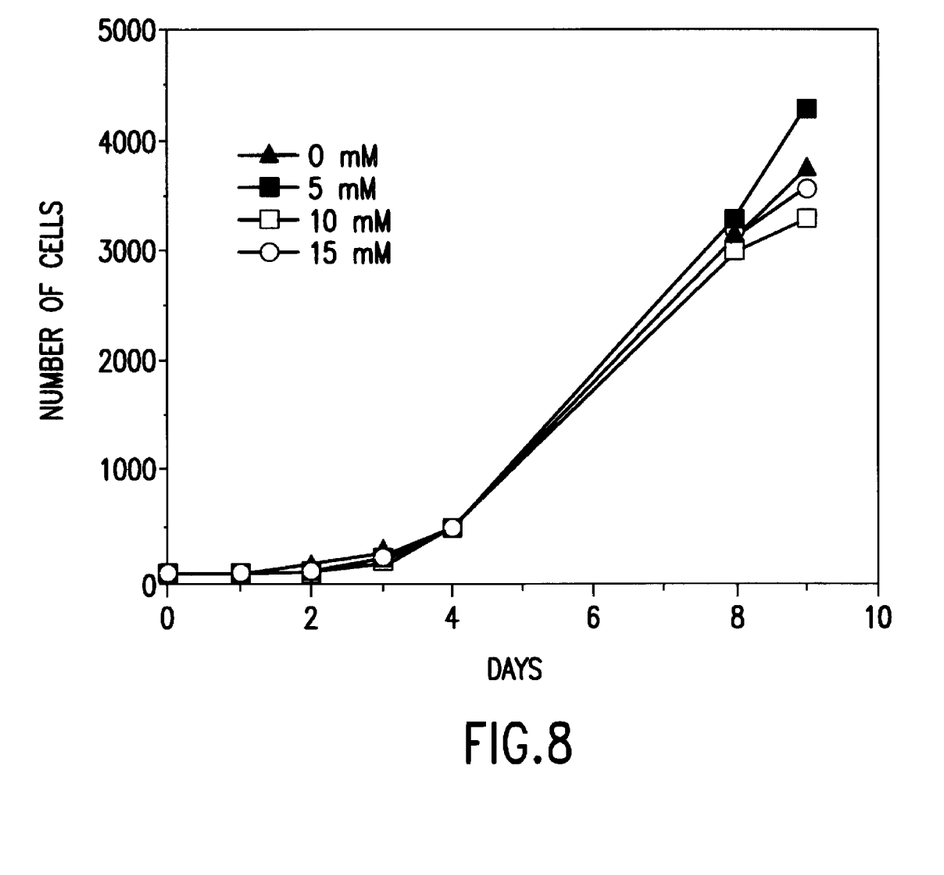
FIG. 8 is a graph showing that WR 151327 does not affect proliferation of U1 cells. Cells were plated at concentrations of $1 \times 10^4$ per ml in 24-well tissue culture plates and the indicated concentrations of WR 151327 were added. The cells were harvested at the indicated time points and counted on a hemocytometer.

Different concentrations of WR 151327 were added to growth medium (RPMI-1640 supplemented with 10% FCS) and the proliferation of U1 cells was monitored by counting cells. Over a period of 7 days, cell proliferation in the presence of 5, 10 or 15 mM WR 151327 was no different than in the untreated control cells (FIG. 8). Viability of cells treated with different doses of WR 151327, determined by trypan blue exclusion, was >95%, for as long as seven days.

6.3. Discussion

The results presented above show that activation of HIV expression in chronically infected promonocytic cells was suppressed by WR 151327, an organic thiophosphate reducing agent with oxygen-free radical scavenging capacity (Grdina et al., 1991, supra). Without killing cells or inhibiting their growth, pretreatment of U1 cells with WR 151327 decreased in a dose-dependent manner the level of RT activity induced by three different agents, TNFα, GM-CSF and PMA. In addition, levels of HIV proteins were similarly reduced.

Similar to N-acetyl cysteine, which suppressed PMA- and TNFα-mediated induction of HIV-LTR transcription by inhibiting NFKB activity (Staal, F. J. et al., 1990, supra), WR 151327 suppressed transcriptional activity of HIV-LTR in transiently transfected RD cells. Both the baseline and TNFα-stimulated transcriptional activity were suppressed. These results agree with previous findings which had shown that reducing agents may suppress the induction of HIV expression in vitro at both transcriptional and post-transcriptional levels (Roederer et al., supra; Kalebic et al., supra Staal et al., supra; Kubota et al.. supra; Harakeh et al., 1990, 1991, supra).

The HIV-inducing activity of TNFα was not altered by directly incubating it with WR 151327, indicating that the suppressive effect of WR 151327 is not due to inactivation of TNFα.

Pretreatment of U1 cells with WR-151327 was required for manifestation of the suppression of induction of HIV expression. This suggests that WR 151327 must first be internalized. While N-acetyl cysteine and glutathione suppressed activation of HIV expression in chronically infected cells induced by IL-6, TNFα, and PMA (Roederer et al., supra; Kalebic et al., supra), WR 151327 also suppressed induction of HIV by GM-CSF.

The observed suppressive effect of WR-151327 on cytokine-induced HIV expression in a chronically infected cell line suggests that WR 151327 will be a useful agent to control chronic stages of HIV infection in patients. It is possible increased levels of cytokines in vivo stimulate replication of latent HIV in chronically infected cells, thereby exacerbating the course of HIV infection.

Based on the present results and those obtained by others (discussed above), it is concluded that the triggering of HIV expression in chronically infected cells can be inhibited by exogenous reducing agents, and that WR 151327 is a potent suppressive agent for HIV expression. Upon administration in vivo, WR 151327 and functional derivatives and analogues thereof could control viral latency and prevent the induction of HIV replication triggered by cytokines and other agents which induce HIV expression.

The existence of consistently decreased level of glutathione and acid soluble thiols in AIDS patients (Buhlet al., supra; Eck, 1989, supra; Staal, F. J., (1992) *Lancet* 339:909–912) associated with increased levels of cytokines which activate HIV expression and induce oxidative stress, provide a rationale for AIDS therapy by replenishment of reducing agents (Droege W. et al., (1992) *Immunol. Today* 13:211–214; Roederer et al., supra; Harakeh et al., supra; Kalebic et al., supra).

At present, anti-retroviral therapy is subject of intense investigation. Several agents, in particular the nucleotide chain terminators, AZT, ddI, ddC interrupt reverse transcription and most likely interfere with early events of viral life cycle. Other agents targeting which target other events in the HIV life cycle, such as interferon-α which may block the release of HIV virions, are also being examined in clinical studies.

The possibility of blocking the activation of latent virus in chronically infected cells such as macrophages, as described herein, offers a new addition to the current armamentarium of anti-HIV drug therapeutic modalities. Alone, or in combination with other reducing agents, WR 151327 is of particular interest. In addition to suppressing cytokine-induced HIV expression in chronically infected cells, as described herein, WR 151327 also decreases the bone marrow toxicity and mutagenic effects of AZT (Green et al.. supra; Grdina, 1992, supra). By virtue of its pleiotropic effects, WR 151327 holds out the promise of contributing significantly to the clinical management of HIV infection.

The references cited above are all incorporated by reference herein, whether specifically incorporated or not.

Having now fully described this invention, it will be appreciated by those skilled in the art that the same can be performed within a wide range of equivalent parameters, concentrations, and conditions without departing from the spirit and scope of the invention and without undue experimentation.

While this invention has been described in connection with specific embodiments thereof, it will be understood that it is capable of further modifications. This application is intended to cover any variations, uses, or adaptations of the invention following, in general, the principles of the invention and including such departures from the present disclosure as come within known or customary practice within the art to which the invention pertains and as may be applied to the essential features hereinbefore set forth as follows in the scope of the appended claims.

What is claimed is:

1. A single agent therapy for inhibiting HIV replication in a subject infected with HIV, comprising administering to the subject an organic thiophosphate selected from the group consisting of $CH_3NH(CH_2)_3NH(CH_2)_3SPO_3H_2$ (WR 151327), $CH_3NH(CH_2)_3NH(CH_2)_3SH$ (WR 151326), an S-ω(ω-aminoalkylamino)alkyl dihydrogen phosphorothioate of the formula $R-NH-(C_nH_{2n})-NH-(C_mH_{2m})-SPO_3H_2$ wherein R is hydrogen or an alkyl group containing 1 to 7 carbon atoms and m and n independently have a value of from 2 to 6, and mixtures thereof, in an amount capable of suppressing expression of HIV proteins in a cell chronically infected with HIV.

2. The therapy according to claim 1, wherein said organic thiophosphate is WR 151327.

3. The therapy according to claim 1, wherein said organic thiophosphate is WR 151326.

4. The therapy according to claim 1, wherein said organic thiophosphate is S-2-(3-aminopropylamino) ethyl dihydrogen phosphorothioate of the formula $NH_2-(CH_2)_3-NH(CH_2)_2-S-PO_3H_2$.

5. The therapy according to claim 1, wherein said organic thiophosphate is administered orally.

6. The therapy according to claim 5, wherein the dose of said organic thiophosphate is between about 20 mg and about 20 g per m² of body surface area.

7. The therapy according to claim 5, wherein the dose of said organic thiophosphate is between about 500 mg and 1500 mg per m² of body surface area.

8. The therapy according to claim 1, wherein said organic thiophosphate is administered intravenously.

9. The therapy according to claim 8 wherein said intravenous administration comprises a drip intravenous infusion.

10. The therapy according to claim 8, wherein the dose of said organic thiophosphate is between about 10 mg and 10 g per m² of body surface area.

11. The therapy according to claim 8, wherein the dose of said organic thiophosphate is between about 250 mg and 750 mg per m² of body surface area.

12. The method according to claim 11, wherein said organic thiophosphate is S-2-(aminopropylamino) ethyl dihydrogen phosphorothioate of the formula $NH_2-(CH_2)_3NH(CH_2)_2-S-PO_3H_2$.

13. A method for treating a subject infected with HIV, comprising administering to the subject an effective amount of at least one organic thiophosphate selected from the group consisting of $CH_3NH(CH_2)_3NH(CH_2)_3SPO_3H_2$ (WR 151327), $CH_3NH(CH_2)_3NH(CH_2)_3SH$ (WR 151326), an S-ω(ω-aminoalkylamino)alkyl dihydrogen phosphorothioate of the formula $R-NH-(C_nH_{2n})-NH-(C_mH_{2m})-SPO_3H_2$ wherein R is hydrogen or an alkyl group containing 1 to 7 carbon atoms and m and n independently have a value of from 2 to 6, and mixtures thereof, capable of suppressing expression of HIV in a cell chronically infected with HIV, with the proviso that AZT is not co-administered to the subject.

14. The method according to claim 13, wherein said organic thiophosphate is WR 151327.

15. The method according to claim 14, wherein said organic thiophosphate is administered intravenously.

16. The method according to claim 15, wherein said intravenous administration comprises a drip intravenous infusion.

17. The method according to claim 15, wherein the dose of said organic thiophosphate is between about 10 mg and 10 g per m² of body surface area.

18. The method according to claim 15, wherein the dose of said organic thiophosphate is between about 250 mg and 750 mg per m² of body surface area.

19. The method according to claim 13, wherein said organic thiophosphate is WR 151326.

20. The method according to claim 13, wherein said organic thiophosphate is administered orally.

21. The method according to claim 20, wherein the dose of said organic thiophosphate is between about 20 mg and about 20 g per m² of body surface area.

22. The method according to claim 20, wherein the dose of said organic thiophosphate is between about 500 mg and 1500 mg per m² of body surface area.

23. A single agent therapy for inhibiting HIV viral and protein expression in a cell chronically infected with HIV, comprising exposing in vivo, said cell to an organic thiophosphate selected from the group consisting of $CH_3NH(CH_2)_3NH(CH_2)_3SPO_3H_2$ (WR 151327), $CH_3NH(CH_2)_3NH(CH_2)_3SH$ (WR 151326), an S-ω(ω-amino-alkylamino) alkyl dihydrogen phosphorothioate of the formula $R-NH-(C_nH_{2n})-NH-(C_mH_{2m})-SPO_3H_2$ wherein R is hydrogen or an alkyl group containing 1 to 7 carbon atoms and m and n independently have a value of from 2 to 6, and mixtures thereof, in an amount capable of suppressing expression of HIV proteins in chronically infected cells.

24. A method for inhibiting HIV viral and protein expression in a cell chronically infected with HIV, comprising exposing in vivo, said cell to at least one organic thiophosphate selected from the group consisting of $CH_3NH(CH_2)_3NH(CH_2)_3SPO_3H_2$ (WR 151327), $CH_3NH(CH_2)_3NH(CH_2)_3SH$ (WR 151326), an S-ω(ω-amino-alkylamino)alkyl dihydrogen phosphorothioate of the formula $R-NH-(C_nH_{2n})-NH-(C_mH_{2m})-SPO_3H_2$ wherein R is hydrogen or an alkyl group containing 1 to 7 carbon atoms and m and n independently have a value of from 2 to 6, and mixtures thereof, in an amount capable of suppressing expression of HIV proteins in chronically infected cells, with the proviso said cell is not co-exposed to AZT.

* * * * *